United States Patent [19]

Barber

[11] Patent Number: 4,904,266
[45] Date of Patent: Feb. 27, 1990

[54] BONE JOINT IMPLANT AND METHOD

[76] Inventor: Forrest C. Barber, P.O. Box 911001, Fort Worth, Tex. 76111

[21] Appl. No.: 212,283

[22] Filed: Jun. 27, 1988

[51] Int. Cl.⁴ ............................................. A61F 2/32
[52] U.S. Cl. .......................................... 623/23; 623/18
[58] Field of Search ...................... 623/16, 18, 19, 20, 623/21, 22, 23

[56] References Cited

U.S. PATENT DOCUMENTS

| | | | |
|---|---|---|---|
| 4,080,666 | 3/1978 | Fixel | 623/23 |
| 4,454,612 | 6/1984 | McDaniel et al. | 623/23 |
| 4,670,015 | 6/1987 | Freeman | 623/23 |
| 4,728,335 | 3/1988 | Jurgutis | 623/23 |
| 4,770,660 | 9/1988 | Averill | 623/23 |

FOREIGN PATENT DOCUMENTS

| | | | |
|---|---|---|---|
| 0146192 | 6/1985 | European Pat. Off. | 623/22 |
| 0179626 | 4/1986 | European Pat. Off. | 623/18 |
| 3334058 | 4/1985 | Fed. Rep. of Germany | 623/22 |

Primary Examiner—Richard J. Apley
Assistant Examiner—David J. Isabella
Attorney, Agent, or Firm—James E. Bradley

[57] ABSTRACT

A prosthetic device is shown for repair or replacement of joints of skeletal bones. The device includes an elongated stem having a linear axis which defines a distal end and a proximal portion. An articulating ball extends outwardly from the proximal portion and is shaped for rotary movement in a socket. A pliable sheath of a synthetic material is slidably received about the elongated stem to thereby form a snugly fitting cover for the stem when the stem is implanted in a cavity in the skeletal bone.

3 Claims, 2 Drawing Sheets

BONE JOINT IMPLANT AND METHOD

BACKGROUND OF THE INVENTION

1. Field of the Invention

The present invention relates generally to artificial bone implants and specifically, to an artificial femoral implant intended to be joined to a live femur to replace a natural bone member which has been surgically resected due to trauma or disease.

2. Description of the Prior Art

The hip joint is constituted by the upper portion of the upper leg bone (femur), which terminates in an offset bony neck surmounted by a ball-headed portion which rotates within a socket (acetabulum) in the hip bone. Replacement of the hip joint by artificial implant is well known in the art, but the prior art implants have suffered from a number of disadvantages.

A conventional hip implant is performed by resecting the neck of the femur and reaming a longitudinal cavity down the femur to receive the stem of an implant. The stem of the implant is usually hammered into place and then cemented, for example, using an acrylic cement, such as methyl methacrylate. It often happens that the stem eventually works loose, either due to faulty cementing or the passage of time. This allows movement of the implant, causing bone erosion. Bone erosion can lead to tissue reactions, which themselves can lead to further bone destruction. The joint itself can then become out of alignment and/or damaged beyond repair. The presence of cement along the entire stem cavity makes removal of the implant for replacement purposes extremely difficult.

SUMMARY OF THE INVENTION

The implant of the invention comprises an elongated stem having a linear axis defining distal and proximal portions. An intermediate portion has one end integral with the stem and extends medially a predetermined length, from said proximal portion. A depth restricting collar joins the intermediate portion. A neck portion extends outwardly from the collar and an articulating ball is attached to the neck portion and shaped for rotary movement in a socket. A pliable sheath of a synthetic material is slidably received about the elongated stem to thereby form a snugly fitting cover for said stem when the stem is implanted in a precisely sized longitudinal aperture in the femur.

In the method of the invention, a pliable sheath of synthetic material is installed about the elongated stem of the implant to form a snugly fitting cover for the stem. An open cavity, including a precisely sized longitudinal aperture is then formed in the femur for receiving the stem of the implant. The stem, with its covering of pliable, synthetic material, can then be implanted within the longitudinal aperture of the femur. Cement can be applied within a portion of the cavity formed within the femur above the stem receiving longitudinal aperture, the stem and snugly fitting pliable sheath serving to restrict the downward flow of cement into the stem receiving aperture of the implant.

The present invention has as its object to provide the least traumatic and most secure bone implant possible which also provides the greatest ease of retraction of the implant stem for replacement.

A further object of the invention is to provide a femoral implant which is devoid of cement within the stem securing aperture of the femur and which can be readily removed and/or replaced.

A further object of the invention is to provide a femoral implant which can be secured in a longitudinal aperture provided in the femur without being driven into the femur by hammering means, as in the case of the prior art.

Another object of the invention is to provide an implementation aperture in the femur which tapers to match the prosthesis stem tightly, surface-to-surface, not requiring cement in the region of the implant surrounding the implant stem.

Additional objects, features and advantages will be apparent in the written description which follows.

BRIEF DESCRIPTION OF THE DRAWING

The novel features believed characteristic of the invention are set forth in the appended claims. The invention itself however, as well as a preferred mode of use, further objects and advantages thereof, will best be understood by reference to the following detailed description of an illustrative embodiment when read in conjunction with the accompanying drawings, wherein:

DETAILED DESCRIPTION OF THE INVENTION

Figure 1:
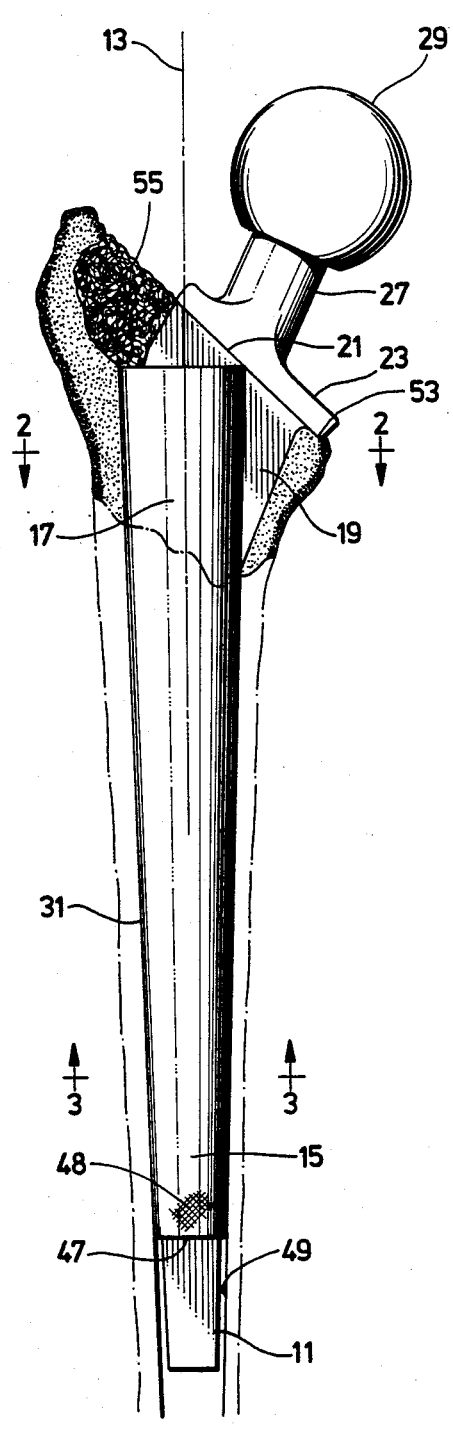
FIG. 1 is a side view of a femur, partially in section, showing the implant of the invention in place within the femur.
Figure 5:
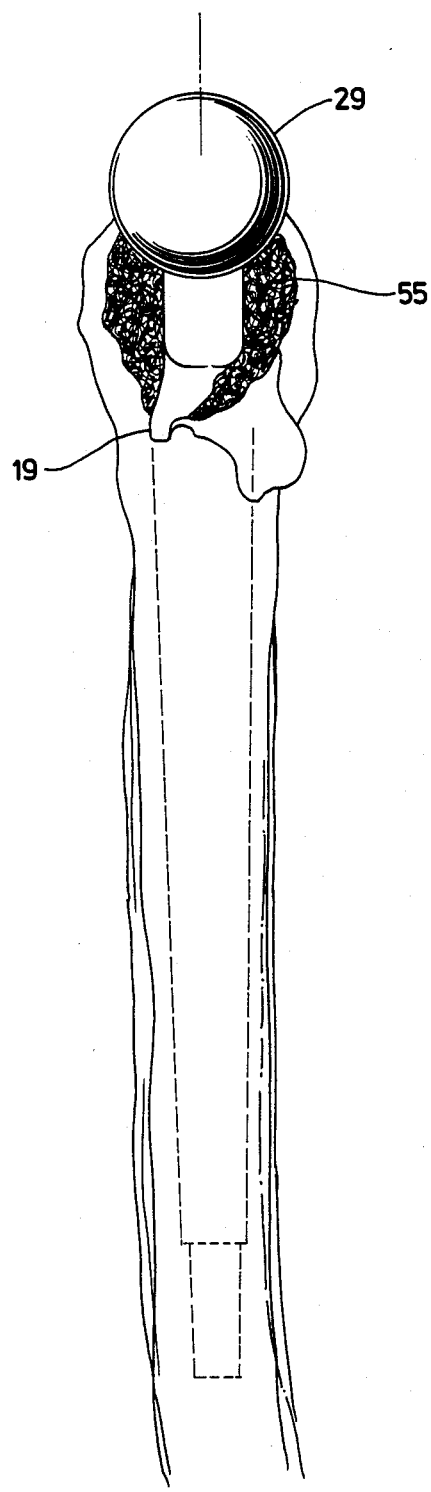
FIG. 5 is a perspective view of, resected femur showing the implant ball, neck and collar portions with cement filling the upper-most portion of the femur cavity.
Figure 4:
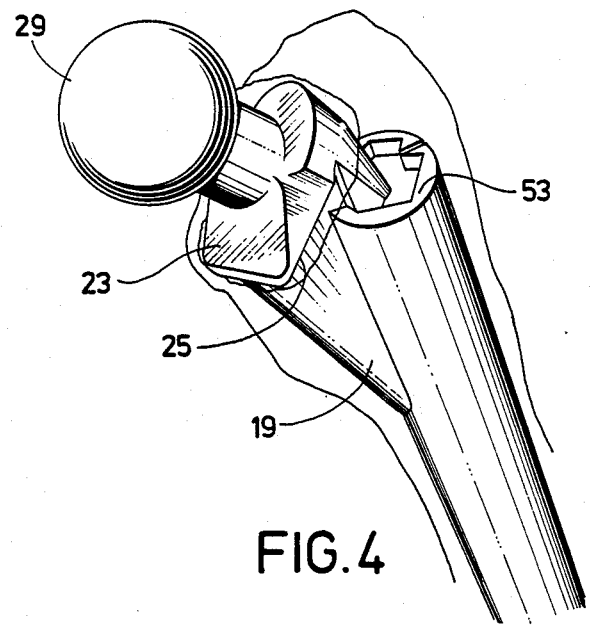
FIG. 4 is an end view of the implant of the invention showing the implant positioned within a resected femur.

As best seen in FIG. 1, the femoral prosthesis of the invention includes an elongated stem 11 having a linear axis 13 which defines distal and proximal portions 15, 17. The stem 11 is axially tapered so that the cross-sectional area decreases in the direction of the distal portion 15.

Figure 2:
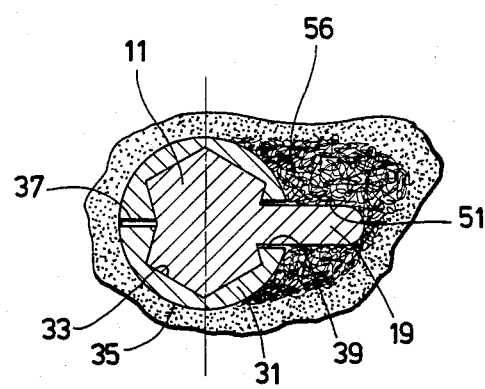
FIG. 2 is a cross-sectional view taken along lines II—II in FIG. 1.

An intermediate portion 19, which is preferably in the shape of a flattened wedge, has one end integral with the stem 11 and extends medially a predetermined length from the proximal portion 17 to an opposite end 21. As seen in FIGS. 1 and 2, the wedge-shaped portion 19 extends outwardly into the lesser trochanter area 56 to restrict rotational movement of the implant.

A depth restricting collar 23 joins the opposite end 21 of the intermediate portion 19 and includes a peripheral lip 25 adapted to mate flushly with the uppermost surface of the resected femur, as shown in FIGS. 1 and 2. Collar 23 forms an acute angle with respect to the linear axis 13 and is generally aligned with the greater trochanter to lesser trochanter in its surgically resected plane.

A femoral neck portion 27 extends outwardly from the upper surface of the depth restricting collar 23. An articulating ball 29 is attached to the neck portion 27 and is shaped for rotary movement in a socket in an acetabulum.

The implant stem 11 is of an acceptable material for introduction to the human body, such as cobalt-chromium alloy or titanium alloy. It can be all of one material or can have a ball 29 of a different material such as ceramic. The surface of the stem 11, or portions thereof, can also be textured, coarse blasted, or coated depending upon the particular application.

Figure 3:
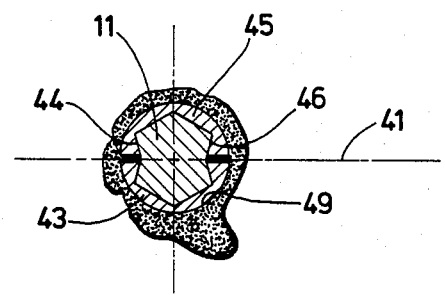
FIG. 3 is a cross-sectional view taken along lines III—III in FIG. 1.

As best seen in FIGS. 1, 2, 3, the stem 11 has a pliable sheath of a synthetic material 31 which is separate from the metallic stem 11 and which is slidably received about a portion of the elongated stem to thereby form a snugly fitting cover for the stem 11 when the stem is implanted in the skeletal bone of the femur. The pliable sheath 31 can be of high density polyethylene, or similar bio-compatible material and is preferably provided in two half-sections, each half-section having an interior 33, an exterior 35 and longitudinal side edges 37, 39. The interior 33 of each half-section of the sheath forms a polygonally shaped recess for engaging the mating polygonally shaped exterior surface of the stem 11. For instance, the axis 41 in FIG. 3 divides the stem into two identical pentagonal shaped portions which are adapted to slidingly engage the mating recesses of the sheath halves 43, 45. The lower sidewalls 44, 46 of each pentagonal shaped portion are inclined inwardly with respect to the the axis 41, forming an acute angle therewith, to thereby engage a mating internal clip region of the sheath half-sections. The exterior surface of the sheath can be provided with a grooved or knurled surface 48 to facilitate bone growth ingression.

The method of installing the bone implant of the invention will now be described. The pliable sheath 31 of synthetic material is first installed about the stem 11 of the implant by sliding each half-section 43, 45 over the stem 11 to thereby form a snugly fitting cover for the stem. As will be noted in FIG. 1, the lowermost extent 47 of the pliable sheath 31 leaves approximately twenty percent of the stem 11 exposed. The stem 11 and sheath 31 are then installed within a mating cavity, including a longitudinal aperture 49, provided within the femur. It will be noted that the aperture 49 is reamed to match the tapered geometrical configuration of the stem and sheath to form a snug fit. It should be possible to slide the stem and sheath into position within the aperture 49 without the use of hammering means and yet achieve a snug fit between the sheath and aperture 49.

As shown in FIG. 2, the wedge-shaped intermediate portion 19 is received within a preformed slot (51 in FIG. 2) in a substantially intact bony neck of the femur. The depth restricting collar 23 is seated substantially directly on the resected surface 53 of the femur. Cement can then be applied within a portion of the cavity formed within the femur above the stem receiving, longitudinal aperture 49. The cemented area is generally the lesser trochanter area (56 in FIG. 2) of the femur up to the level of the collar 23.

An invention has been provided with several advantages. The artificial femoral implant of the invention can be joined to a live femur to replace a natural bone member which has been surgically resected due to trauma or disease. The implant of the invention is devoid of stem cement which weakens in time and fails to allow for ease of extraction when implant revisions are required. Cement is used only in the greater trochanter to lesser trochanter area to maintain stem position until femur to stem bone growth occurs. The lack of cement along the implant stem improves the chances for timely bone growth ingression along the implant.

The lack of stem cement allows stem retraction with minimal cement removal should stem extraction prove necessary. A broken implant can be removed by minimal cement removal at the trochanters followed by slidably retracting the implant stem from its plastic cover before removal of the bone ingressed plastic cover.

The method of the invention provides a new and improved method for treating fractures of the femoral head, allowing early mobilization of the patient after fixation. The implant can be secured in a snug manner within the femoral cavity without being driven into the femur by hammering. Because forceful hammering is not required, the chances of splitting the shaft, femoral neck, or trochanter is reduced.

The combination of the sheathed stem and mating aperture in the femur together with the wedge-shaped intermediate portion of the stem and depth restricting shelf provide an implant which requires only minimal cementing in the trochanters to provide a securely bound implant.

While the invention has been shown in only one of its forms, it is not thus limited, but is susceptible to various changes and modifications without departing from the spirit thereof.

What is claimed is:

1. A prosthetic device for repair or replacement of joints of skeletal bones, by implantation in skeletal bone, said prosthetic device comprising:
    an elongated stem having a linear axis defining distal and proximal portions;
    an intermediate portion having one end integral with said stem and extending medially a predetermined length from said proximal portion;
    a depth restricting collar joining said intermediate portion;
    a neck portion extending outwardly from said collar;
    an articulating ball attached to said neck portion and shaped for rotary movement in a socket;
    a pliable sheath of a synthetic material which is slidably received about said elongated stem to thereby form a snugly fitting cover for said stem when said stem is implanted in said skeletal bone;
    wherein said pliable sheath comprises two half-sections which are slidably received about the exterior surface of said stem; and
    wherein said sheath half-sections each have an interior, an exterior and longitudinal side edges, said edges being slidably retained within mating recesses provided on the exterior surface of said stem.

2. A method of introducing to a human body a hip implant for use in a femur having a resected surface, the implant including an elongated stem having a linear axis defining distal and proximal portions, a flattened wedge-shaped portion of thickness less than that of the adjacent stem portion and having one end integral with said stem and extending medially a predetermined length from said proximal portion to an opposite end, a depth restricting collar joining said flattened wedge-shaped portion, a neck portion extending outwardly from said collar, and an articulating ball attached to said neck portion, said ball being shaped for rotary movement in a socket in an acetabulum, the method comprising the steps of:
    installing a pliable sheath of a synthetic material about said elongated stem to thereby form a snugly fitting cover for said stem;
    forming an open cavity, including a precisely sized longitudinal aperture in said femur for receiving said stem;

providing a preformed slot in said femur of a size to receive said flattened wedge-shaped portion of said implant;

sliding said stem with its pliable sheath of synthetic material into said previously formed aperture in said femur, whereby, when said stem is implanted, said wedge-shaped portion is received in said preformed slot in a substantially intact bony neck of said femur, said depth restricting collar being seated subtantially directly on said resected surface of said femur; and applying a cement within a portion of the cavity formed within said femur above said stem receiving longitudinal aperture, the stem and snugly fitting pliable sheath serving to restrict the downward flow of cement into the stem receiving aperture of said implant.

3. A method of introducing to a human body a hip implant for use in femur having a resected surface, the implant including an elongated stem having a linear axis defining distal and proximal portions, a flattened wedge-shaped portion of thickness less than that of the adjacent stem portion and having one end integral with said stem and extending medially a predetermined length from said proximal portion to an opposite end, a depth restricting collar joining said flattened wedge-shaped portion, a neck portion extending outwardly from said collar, and an articulating ball attached to said neck portion, said ball being shaped for rotary movement in a socket in an acetabulum, the method comprising the steps of:

installing a pliable sheath of a synthetic material about said elongated stem to thereby form a snugly fitting cover for said stem;

forming an open cavity, including a precisely sized longitudinal aperture in said femur for receiving said stem;

providing a preformed slot in said femur of a size to receive said flattened wedge-shaped portion of said implant;

sliding said stem with its pliable sheath of synthetic material into said previously formed aperture in said femur, whereby, when said stem is implanted, said wedge-shaped portion is received in said preformed slot in a substantially intact bony neck of said femur, said depth restricting collar being seated substantially directly on said resected surface of said femur; and wherein said pliable sheath of synthetic material is provided as half-sections, each half section having an interior, and exterior and longitudinal side edges, and wherein said sheath is installed on said stem by sliding said side edges of said half-sections into mating recesses provided on the exterior surface of said stem to thereby form a snugly fitting cover for said stem.

* * * * *